United States Patent [19]

Sherba et al.

[11] Patent Number: 5,212,193
[45] Date of Patent: May 18, 1993

[54] ANTIMICROBIAL COMPOSITIONS COMPRISING 3,4-DICHLOROANILIDES AND ISOTHIAZOLONES AND METHODS OF CONTROLLING MICROBES

[75] Inventors: Samuel E. Sherba, Willingboro, N.J.; Raj J. Mehta, Gujarat, India

[73] Assignee: Rohm and Haas Company, Philadelphia, Pa.

[21] Appl. No.: 672,305

[22] Filed: Mar. 20, 1991

[51] Int. Cl.$^5$ .................. A01N 37/18; A01N 43/80
[52] U.S. Cl. .................... 514/372; 162/161; 210/724; 514/629
[58] Field of Search ............... 514/372, 629; 162/161; 210/724

[56] References Cited

U.S. PATENT DOCUMENTS

| | | | |
|---|---|---|---|
| 3,108,038 | 10/1963 | Fielding et al. | 514/629 |
| 4,173,643 | 11/1979 | Law | 514/372 |
| 4,265,899 | 5/1981 | Lewis et al. | 514/372 |

OTHER PUBLICATIONS

Hodogaya, C. A. vol. 94 (1981) 94: 26143q.
Tanaka et al., C.A. vol. 84 (1976) 84: 1245e.
S. D. Strauss et al., J. Powewr, S1, 1984.
F. C. Kull et al., Applied Microbiology 9, 538 (1961).

Primary Examiner—Allen J. Robinson
Attorney, Agent, or Firm—Michael B. Fein

[57] ABSTRACT

A synergistic antimicrobial composition comprising a 2-alkyl-3-isothiazolone and a 3,4-dichloroanilide of the formula

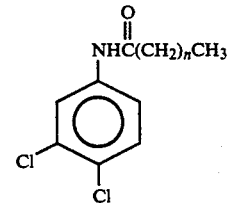

where n is an integer from 1 to 2, in a ratio to each other which exhibits synergism is disclosed.

15 Claims, No Drawings

ANTIMICROBIAL COMPOSITIONS COMPRISING 3,4-DICHLOROANILIDES AND ISOTHIAZOLONES AND METHODS OF CONTROLLING MICROBES

BACKGROUND OF THE INVENTION

1. Field of the Invention

The present invention relates to antimicrobial compositions and methods of controlling microbes.

2. Description of the Prior Art

The presence of microbes in various aqueous systems such as latices, paints, coatings, cooling water systems, decorative ponds and the like, can cause deterioration or disfigurement of these systems. For example, painted surfaces may be disfigured by the unsightly buildup of microbes, thus detracting from the overall aesthetics of the painted article; cooling towers may lose efficiency due to the buildup of microbes on surfaces, thus reducing the heat transfer capabilities of the tower. It is conventional to practice methods which inhibit the microbial deterioration of such systems by incorporating a variety of additives or combination of additives that are characterized by having antimicrobial activity.

A wide variety of materials have been used to control microbes in different environments, some of which are: chlorine/bromine compounds, glutaraldehyde, isothiazolones, organotin formulations, copper salts, quaternary ammonium compounds (SD Strauss and PR Puckorius in *J. Power*, S1, June 1984), and triazines. Each has deficiencies related to toxicity, pH and temperature sensitivity, limited effectiveness, chemical stability, and/or compatibility.

Substituted anilides, e.g., 3,4-dichloropropionanilides, are known herbicides, but are not known for their antimicrobial properties.

Based on the aforementioned performance deficiencies of conventional antimicrobial compounds there is a need for more effective antimicrobial agents that can be used at lower dosage rates, thus being more cost effective for the end user, reducing the pollution load on the affected environmental systems, and reducing the side effects to nearby non-target organisms, such as fish, useful crops, etc.

SUMMARY OF THE INVENTION

It is an object of this invention to provide a method of controlling microbes at very low levels of active ingredient. It is a further object to use compositions which are compatible with a variety of systems susceptible to deterioration by microbes. Another object is to provide a method of controlling microbes in cooling towers, paints, marine antifoulant coatings, spray washes, swimming pools, coatings, decorative ponds, fabric, leather, paper, wood, metal working fluids, cosmetic formulations, fuel systems, therapeutic pharmaceutical formulations and the like, without objectionable by-product odors, discoloration, or otherwise detrimental effects on the treated (and controlled) systems. These objects, and others which will become apparent from the following disclosure, are achieved by the present invention which is, in one aspect a composition useful for controlling microbes comprising (A) a 2-alkyl-3-isothiazolone of the formula

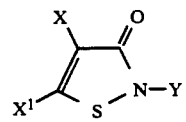

wherein

Y is a $(C_5-C_{12})$alkyl or a $(C_5-C_8)$cycloalkyl;

X is hydrogen, halogen, or $(C_1-C_4)$alkyl; and $X^1$ is hydrogen, halogen, or $(C_1-C_4)$alkyl;

and (B) a 3,4-dichloroanilide of the formula

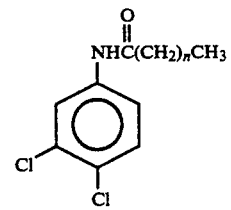

wherein n=1 or 2, in a ratio to each other which exhibits synergism.

In another aspect, the invention comprises a method for inhibiting the growth of a member selected from the group consisting of bacteria, fungi, algae and mixtures thereof in a locus subject to contamination by said member, which comprises incorporating onto or into the locus, in an amount which is effective to adversely affect the growth of said member, the aforementioned composition.

Another aspect of the invention is a method of controlling microbes in cooling tower water comprising maintaining a concentration of the aforementioned composition in the water.

The invention also comprises microbe-resistant coating or impregnant compositions and marine antifoulant compositions comprising the antimicrobial composition.

DETAILED DESCRIPTION OF THE INVENTION AND THE PREFERRED EMBODIMENTS

We have discovered an especially effective composition useful for controlling microbes comprising (A) a 2-alkyl-3-isothiazolone of the formula

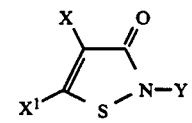

wherein

Y is a $(C_5-C_{12})$alkyl or a $(C_5-C_8)$cycloalkyl;

X is hydrogen, halogen, or $(C_1-C_4)$alkyl; and $X^1$ is hydrogen, halogen, or $(C_1-C_4)$alkyl;

and (B) a 3,4-dichloroanilide of the formula

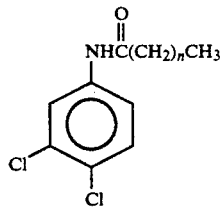

(II)

wherein n=1 or 2, in a ratio to each other which exhibits synergism.

The preferred isothiazolones are 4,5-dichloro-2-n-octyl-3-isothiazolone (I,Y=n-octyl, X and $X^1$=chlorine) and 2-n-octyl-3-isothiazolone (I,Y=n-octyl, X and $X^1$=hydrogen).

In accordance with the invention a method of controlling microbes comprises using an effective amount of the aforementioned composition.

In contrast to the 3,4-dichloroanilides of formula II where n=1 or 2 (3,4-dichloropropionanilide and 3,4-dichlorobutyranilide, respectively), those anilides where n=4 or greater do not provide combinations with the isothiazolones of formula I which are synergistic; in fact, several of these particular combinations are antagonistic towards one another in terms of antimicrobial activity (see Examples 3-6).

Another important utility is in imparting microbial resistance to a coating or impregnant composition comprising incorporation of the composition of the invention in the coating or impregnant, preferably at a concentration of about 0.1 ppm to about 2 percent, more preferably at concentration of about 1 ppm to 1 percent, and most preferably at a concentration of about 10 to 4000 ppm.

Algae-resistant coating or impregnant compositions provided by the invention preferably comprise about 0.1 ppm to about 2 percent of the antimicrobial composition, more preferably about 10 to 4000 ppm.

In a marine antifoulant composition, on the other hand, the antimicrobial composition of the invention comprises about 1 to 10 percent of the antifoulant composition.

In a therapeutic pharmaceutical formulation, e.g., lotion, cream, ointment or topical treatment; in the treatment of metal working fluids; and in the protection of fabric, leather, paper or wood materials, the microbicidal composition is added at a concentration of from about 0.1 ppm to about 2 percent by weight. In aqueous media, the microbial composition comprises from about 0.1 ppm to about 1 percent of the aqueous system depending on the specific end use; for examples, in cooling water tower applications and with pulp or paper manufacturing processes, the microbicidal composition is added at a concentration from about 0.1 to about 1000 ppm by weight. In cosmetic formulations, e.g., face or hand creams, toiletries, etc; and in the treatment of fuel systems, e.g., jet fuel, gasoline, heating oil, etc., the microbicidal composition is added at a concentration of from about 0.1 ppm to about 1 percent by weight.

The microbial resistant compositions can also be used in construction products such as stucco, roof mastics, wall mastics, and masonry coatings for algae protection; in clear finishes and coatings to protect underlying substrates from algae; for algae control in aquaculture, including aquaria, fish hatcheries, shrimp ponds, finfish ponds, mollusc and crustacean cultivation; for algae control in recreational and decorative bodies of water such as swimming pools, lakes, fountains and decorative ponds; for algae control in bodies of water for industrial or municipal use, such as settling or separation ponds, waste treatment ponds, and water reservoirs; for algae control in hydroponic farming; for algae control in processing and manufacture of pulp and paper products; for inclusion in plastics or in coatings for plastics to protect against algae; and in plastics or coatings for plastics for swimming pool liners.

We prefer antimicrobial compositions wherein the weight ratio of (A) to (B) is about 0.01/100 to about 100/1. A preferred ratio range is from about 0.03/100 to about 1/10 by weight. Particularly preferred ratio ranges are from about 0.5/100 to about 1/25 and from about 0.1/100 to about 1/10 depending upon the particular isothiazolone/3,4-dichloroanilide combination in use.

The following examples represent just a few of the many uses and compounds of the invention. They are intended to be illustrative but not limiting. Various modifications, alternatives, and improvements should become apparent to those skilled in the art without departing from the spirit and scope of the invention.

EXAMPLES

A. General Procedure

MIC values represent the Minimum Inhibitory Concentration. This is defined as the lowest level of compound required to completely inhibit (repress) the growth of a given organism.

A synergistic effect is defined as the response of two variables which is greater than the sum of both parts alone. Synergy was determined from combination studies with two compounds by the method of calculation described by F. C. Kull, P. C. Eisman, H. D. Sylwestrowicz and R. K. Mayer, *Applied Microbiology* 9,538 (1961):

$$\frac{Q_A}{Q_a} + \frac{Q_B}{Q_b} = \text{synergism index (SI)}$$

where:

$Q_a$=quantity of compound A, acting alone, producing an end point (MIC)

$Q_A$=quantity of compound A, in mixture, producing an end point (MIC)

$Q_b$=quantity of compound B, acting alone, producing an end point (MIC)

$Q_B$=quantity of compound B, in mixture, producing an end point (MIC)

The following SI values may be attained:

SI>1 represents antagonistic effect,

SI=1 represents additive effect,

SI<1 represents synergy.

Efficacy studies were conducted on a variety of microorganisms with fatty acids and isothiazolone mixtures. The MIC studies were conducted using microtiter plate assays. In this method, a wide range of concentrations was tested by preparing two-fold serial dilutions of the compound in 96-well plastic microtitier plates. All liquid media transfers were performed with calibrated single or multichannel digital pipetters. Stock solutions of compounds were prepared in appropriate solvents and dispensed to the growth medium. All subsequent dilutions in plates were made using the desired growth medium; total volume of liquid in each well was 100 µl. Each plate contained a concentration of both compounds made by serially titrating equal volumes of liquids in two directions in the microtiter plate. Each plate contained a control row for each combination (one component only), hence, the individual compound MIC values were also determined.

B. Isothiazolone Structure

Isothiazolones included in the examples are designated as follows:
1) Isothiazolone A: 4,5-dichloro-2-n-octyl-3-isothiazolone
2) Isothiazolone B: 2-n-octyl-3-isothiazolone

C. Anilide Structure 3,4-Dichloroanilides evaluated for microbicidal activity in combination with Isothiazolones A and B included those according to formula II where n=1 (3,4-dichloropropionanilide, Anilide A)
n=2 (Anilide B, 3,4-dichlorobutyranilide)
n=4 (Anilide C)
n=5 (Anilide D)
n=6 (Anilide E)
n=8 (Anilide F)

EXAMPLE 1

Using a pure culture of *Aspergillus niger*, various combinations of Anilide A (Compound B) and Isothiazolone A (Compound A) were subjected to MIC determinations in mycophil broth.

| Qa | Qb | Qa/Qb | SI |
|---|---|---|---|
| 0 | 125 ($Q_b$) | 0 | 1.0 |
| 0.31 | 64 | 1/206 | 0.75 |
| 0.62 | 32 | 2/98 | 0.75 |
| 0.62 | 16 | 4/96 | 0.63 |
| 0.62 | 8 | 7/93 | 0.56 |
| 0.62 | 4 | 13/87 | 0.53 |
| 1.25 ($Q_A$) | 0 | — | 1.0 |

EXAMPLE 2

Using a pure culture of *Aspergillus niger*, various combinations of Anilide B (Compound B) and Isothiazolone A (Compound A) were subjected to MIC determinations in mycophil broth.

| Qa | Qb | Qa/Qb | SI |
|---|---|---|---|
| 0 | 250 ($Q_B$) | — | 1.0 |
| 0.62 | 125 | 1/195 | 0.75 |
| 1.25 | 62 | 2/98 | 0.75 |
| 1.25 | 31 | 4/96 | 0.63 |
| 2.5 ($Q_A$) | 0 | — | 1.0 |

EXAMPLE 3 (COMPARATIVE)

Using a pure culture of *Aspergillus niger*, various combinations of Anilide C (Compound B) and Isothiazolone A (Compound A) were subjected to MIC determinations in mycophil broth.

| Qa | Qb | Qa/Qb | SI |
|---|---|---|---|
| 0 | >1000 ($Q_B$) | — | 1.0 |
| 10 | 500 | 2/98 | >8 |
| 5 | 500 | 1/99 | >4 |
| 10 | 250 | 4/96 | >8 |
| 5 | 250 | 2/98 | >4 |
| 10 | 125 | 7/93 | >8 |
| 5 | 125 | 4/96 | >4 |
| 2.5 | 125 | 2/98 | >2 |
| 10 | 64 | 14/86 | >8 |
| 5 | 64 | 7/93 | >4 |
| 2.5 | 64 | 4/96 | >2 |
| 1.25 | 64 | 2/98 | >1 |
| 1.25 ($Q_A$) | 0 | — | 1.0 |

EXAMPLE 4 (COMPARATIVE)

Using a pure culture of *Aspergillus niger*, various combinations of Anilide D (Compound B) and Isothiazolone A (Compound A) were subjected to MIC determinations in mycophil broth.

| Qa | Qb | Qa/Qb | SI |
|---|---|---|---|
| 0 | >1000 ($Q_B$) | — | 1.0 |
| 5 | 250 | 2/98 | >2 |
| 5 | 125 | 4/96 | >2 |
| 2.5 | 125 | 2/98 | >1 |
| 5 | 64 | 7/93 | >2 |
| 2.5 | 64 | 4/96 | >1 |
| 5 | 32 | 14/86 | >2 |
| 2.5 | 32 | 7/93 | >1 |
| 2.5 ($Q_A$) | 0 | — | 1.0 |

EXAMPLE 5 (COMPARATIVE)

Using a pure culture of *Aspergillus niger*, various combinations of Anilide E (Compound B) and Isothiazolone A (Compound A) were subjected to MIC determinations in mycophil broth.

| Qa | Qb | Qa/Qb | SI |
|---|---|---|---|
| 0 | >1000 ($Q_B$) | — | 1.0 |
| 10 | 500 | 2/98 | >4 |
| 10 | 250 | 4/96 | >4 |
| 5 | 250 | 2/98 | >2 |
| 10 | 125 | 7/93 | >4 |
| 5 | 125 | 4/96 | >2 |
| 2.5 | 125 | 2/98 | >1 |
| 10 | 64 | 14/86 | >4 |
| 5 | 64 | 7/93 | >2 |
| 2.5 | 64 | 4/96 | >1 |
| 2.5 ($Q_A$) | 0 | — | 1.0 |

EXAMPLE 6 (COMPARATIVE)

Using a pure culture of *Aspergillus niger*, various combinations of Anilide F (Compound B) and Isothiazolone A (Compound A) were subjected to MIC determinations in mycophil broth.

| Qa | Qb | Qa/Qb | SI |
|---|---|---|---|
| 0 | >1000 ($Q_B$) | — | 1.0 |
| 10 | 250 | 4/96 | >4 |
| 10 | 125 | 7/93 | >4 |
| 5 | 125 | 4/96 | >2 |
| 10 | 64 | 14/86 | >4 |
| 5 | 64 | 7/93 | >2 |
| 10 | 32 | 24/76 | >4 |
| 5 | 32 | 14/86 | >2 |
| 2.5 | 32 | 7/93 | >1 |
| 2.5 ($Q_A$) | 0 | — | 1.0 |

EXAMPLE 7

Using a pure culture of *Aureobasidium pullalans*, various combinations of Anilide A (Compound B) and Isothiazolone A (Compound A) were subjected to MIC determinations in mycophil broth, pH=5.0.

| Qa | Qb | Qa/Qb | SI |
|---|---|---|---|
| 0 | 250 ($Q_B$) | — | 1.0 |
| 0.16 | 125 | 1/3120 | 0.63 |
| 0.32 | 125 | 1/1560 | 0.75 |
| 1.25 ($Q_A$) | 0 | — | 1.0 |

EXAMPLE 8

Using a pure culture of *Aureobasidium pullalans*, various combinations of Anilide A (Compound B) and Isothiazolone B (Compound A) were subjected to MIC determinations in mycophil broth, pH=5.0.

| Qa | Qb | Qa/Qb | SI |
|---|---|---|---|
| 0 | 250 ($Q_B$) | — | 1.0 |
| 0.16 | 125 | 1/800 | 0.56 |
| 0.32 | 125 | 1/400 | 0.63 |
| 0.64 | 125 | 1/200 | 0.75 |
| 1.25 | 64 | 2/98 | 0.75 |
| 1.25 | 32 | 4/96 | 0.63 |
| 1.25 | 16 | 7/93 | 0.56 |
| 1.25 | 8 | 14/86 | 0.53 |
| 2.5 ($Q_A$) | 0 | — | 1.0 |

We claim:

1. A microbial composition comprising a synergistic mixture a first component of which is a 2-alkyl-3-isothiazolone selected from the group consisting of 4,5-dichloro-2-n-octyl-3-isothiazolone and 2-n-octyl-3-isothiazolone

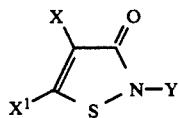

wherein

Y is a ($C_5$-$C_{12}$)alkyl or a ($C_5$-$C_8$)cycloalkyl;

X is hydrogen, halogen, or ($C_1$-$C_4$)alkyl; and $X^1$ is hydrogen, halogen, or ($C_1$-$C_4$)alkyl;

and a second component of which is a 3,4-dichloroanilide of the formula

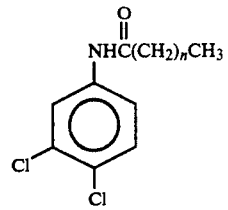

wherein n=1 or 2, wherein the weight ratio of the first component to the second component is in a range of from about 0.03/100 to about 1/10.

2. A coating or impregnant composition comprising from about 0.1 ppm to about 2 percent by weight of the composition of claim 1.

3. A marine antifoulant composition comprising about 1-10 percent by weight of the composition of claim 1.

4. A therapeutic pharmaceutical composition comprising from about 0.1 ppm to about 2 percent by weight of the composition of claim 1.

5. A method for inhibiting the growth of fungi in a locus subject to fungal contamination, which comprises incorporating onto or into the locus, in an amount which is effective to adversely affect the growth of said fungi, the composition of claim 1.

6. The method of claim 5 wherein the locus is an aqueous medium and the composition is used in an amount from about 0.1 ppm to about 1 percent by weight.

7. The method of claim 5 wherein the locus is a coating or impregnant composition and the composition of claim 1 is used in an amount from about 0.1 ppm to about 2 percent by weight.

8. The method of claim 5 wherein the locus is a marine antifoulant composition and the composition of claim 1 is used in an amount from about 1 to about 10 percent by weight.

9. The method of claim 5 wherein the locus is a pulp or paper manufacturing process and the composition is used in an amount from about 0.1 ppm to about 1000 ppm by weight.

10. The method of claim 5 wherein the locus is cooling tower water and the composition is used in an amount from about 0.1 ppm to about 1000 ppm by weight.

11. The method of claim 5 wherein the locus is a metal working fluid and the composition is used in an amount from about 0.1 ppm to about 2 percent by weight.

12. The method of claim 5 wherein the locus is fabric, leather, paper or wood and the composition is used in an amount from about 0.1 ppm to about 2 percent by weight.

13. The method of claim 5 wherein the locus is a cosmetic formulation and the composition is used in an amount from about 0.1 ppm to about 1 percent by weight.

14. The method of claim 5 wherein the locus is a fuel system and the composition is used in an amount from about 0.1 ppm to about 1 percent by weight.

15. The method of claim 5 wherein the locus is a topical therapeutic pharmaceutical formulation and the composition is used in an amount from about 0.1 ppm to about 2 percent by weight.

* * * * *